United States Patent
Assaraf et al.

(10) Patent No.: US 10,767,186 B2
(45) Date of Patent: Sep. 8, 2020

(54) ORGANIC COMPOUNDS

(71) Applicant: Novartis AG, Basel (CH)

(72) Inventors: Yehuda G. Assaraf, D.n. Misgav (IL); Thomas Jostock, Neuenburg am Rhein (DE); Hans-Peter Knopf, Schallstadt (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/233,726

(22) Filed: Aug. 10, 2016

(65) Prior Publication Data

US 2016/0355828 A1 Dec. 8, 2016

Related U.S. Application Data

(63) Continuation of application No. 14/275,304, filed on May 12, 2014, now abandoned, which is a continuation of application No. 13/495,043, filed on Jun. 13, 2012, now abandoned, which is a continuation of application No. 12/808,704, filed as application No. PCT/EP2008/068046 on Dec. 19, 2008, now abandoned.

(30) Foreign Application Priority Data

Dec. 21, 2007 (EP) .................................... 07150326

(51) Int. Cl.
| | |
|---|---|
| *C12N 15/85* | (2006.01) |
| *C12N 15/64* | (2006.01) |
| *C07K 14/705* | (2006.01) |
| *C12N 15/10* | (2006.01) |
| *C07K 16/00* | (2006.01) |
| *C12N 15/65* | (2006.01) |
| *C12P 21/00* | (2006.01) |

(52) U.S. Cl.
CPC ............ *C12N 15/64* (2013.01); *C07K 14/705* (2013.01); *C07K 16/00* (2013.01); *C12N 15/1079* (2013.01); *C12N 15/65* (2013.01); *C12N 15/85* (2013.01); *C12P 21/00* (2013.01); *C07K 2317/14* (2013.01)

(58) Field of Classification Search
None
See application file for complete search history.

(56) References Cited

U.S. PATENT DOCUMENTS 5,965,417 A 10/1999 Uclaf

FOREIGN PATENT DOCUMENTS

| WO | 2004/081167 A2 | 9/2004 |
|---|---|---|
| WO | 2006/059323 A2 | 6/2006 |

OTHER PUBLICATIONS

Yang et al: "The folate receptor alpha is frequently overexpressed in osteosarcoma samples and plays a role in the uptake of the physiologic substrate 5-methyltetrahydrofolate", Clinical Cancer Research, 13(9):2557-2567 (2007).
Bottero et al: "Gene transfection and expression of the ovarian carcinoma marker folate binding protein on NIH/3T3 cells increases cell growth in vitro and in vivo", Cancer Research 53:5791-5796 (1993).
Matuse et al: "Folate receptor allows cells to grow in low concentrations of 5-methyltetrahydrofolate", Proc. Natl. Acad. Sci. USA 89:6006-6009 (1992).
Stempack et al: "Cell and stage of transformation-specific of folate deficiency on methinonine cycle intermediates and DNA methylation in an in vitro model", Carcinogenesis 26:981-990 (2005).
Assaraf et al: "Identification of methotrexate transport deficiency in mammalian cells using fluoresceinated methotrexate and flow cytometry", Prc. Natl. Acad. Sci. USA, 84:7154-7158 (1987).
Rothem et al: "The reduced folate carrier gene is a novel selectable marker for recombinant protein overexpression", Mol Pharmacol, 68:616-624 (2005).
Salazar et al: "The folate receptor: what does it promise in tissue-targeted therapeutics?", Cancer Metastasia Rev. 26:141-152 (2007).
Zhu et al: "The rate of folate receptor alpha (FRalpha) synthesis in folate depleted CHL cells in regulated by a translational mechanism sensitive to media folate levels, while stable overexpression of its mRNA is mediated by gene amplification and an increase in transcript half-life", Journal of Cellular Biochemistry, 81(2)205-219 (2001).
Ramamoorthy et al: "Insilco analysis of functionally important residues in folate receptors", Bioinformation by Biomedical Information Publishing Group, 2(4) 157-162 (2007).
Genbank AAP36649—2003.
Genbank AAA35621—1993.
Senbank AAI41506—2007.

*Primary Examiner* — Celine X Qian
(74) *Attorney, Agent, or Firm* — Linyu L. Mitra

(57) ABSTRACT

The present invention relates to a novel selection system for use in a eukaryotic cell culture process and for expression of a recombinant product of interest. The selection system is based on the introduction of an exogenous functional membrane-bound folate receptor gene together with the polynucleotide or gene encoding the product of interest into a eukaryotic cell and can be widely utilized with eukaryotic cells for which cellular viability is dependent upon folic acid uptake.

17 Claims, No Drawings
Specification includes a Sequence Listing.

ORGANIC COMPOUNDS

This is a continuation of application Ser. No. 12/808,704 filed on Jun. 17, 2010, which is a National Stage of International Application No. PCT/EP2008/068046 filed on Dec. 19, 2008, which claims priority under 35 U.S.C. § 119 to EP Application Serial No. 07150326.2 filed Dec. 21, 2007, each of which applications in its entirety is herein incorporated by reference.

FIELD OF THE INVENTION

The present invention relates to a novel selection system for use in a eukaryotic cell culture process and for expression of a recombinant product of interest. The selection system is based on the introduction of an exogenous functional membrane-bound folate receptor gene together with the polynucleotide or gene encoding the product of interest into a eukaryotic cell and can be widely utilized with eukaryotic cells for which cellular viability is dependent upon folic acid uptake.

BACKGROUND OF THE INVENTION

Selection markers and selection systems are widely used in genetic engineering, recombinant DNA technology and production of recombinant products, for example antibodies, hormones and nucleic acids, in eukaryotic cell culture. The primary goal of such dominant selection markers and selection systems is to introduce a selectable gene which upon exposure to selective growth conditions provides cells capable of high-level production of the recombinant products of interest.

To date, there are 3 major selection marker systems available:

(a) The glutamine synthetase system: The enzyme glutamine synthetase (GS) is responsible for the biosynthesis of glutamine from glutamate and ammonia. This biosynthetic reaction provides the sole pathway for glutamine formation in mammalian cells. Thus, in the absence of glutamine in the growth medium, the enzyme GS is essential for the survival of mammalian cells in culture. Importantly, certain mammalian cell lines including mouse myeloma cells lack the expression of sufficient GS and thus cannot survive without exogenously added glutamine. Hence, such a cell line is an suitable acceptor for a transfected GS gene that in this system can function as a selectable marker that allows for cell growth in a medium lacking glutamine. In contrast, cell lines such as the widely used Chinese hamster ovary (CHO) cells express sufficient GS to support growth in glutamine-free medium. Therefore, if these CHO cells are to be used as the recipient cells for the transfection of the GS gene, the specific and potent GS inhibitor methionine sulfoximine (MSX) can be applied in order to inhibit endogenous GS activity such that only transfectants expressing high levels of the transfected GS gene can survive in a glutamine-free medium. A major disadvantage of the GS system is the relatively long time (i.e. 2-6 months) of selective growth in order to establish cells stably overexpressing the target gene of interest. Another disadvantage is the frequent utilization of the cytotoxic agent MSX for the augmentation of the selective pressure. The presence of such a cytotoxic agent along with a recombinant product of interest (e.g. a polypeptide like an antibody) may require additional purification steps to rid of this cytotoxic agent.

(b) The dihydrofolate reductase/MTX selection system: Dihydrofolate reductase (DHFR) catalyzes the NADP-dependent reduction of dihydrofolic acid to tetrahydrofolic acid (THF). THF is then interconverted to 10-formyl-THF and 5,10-methylene-THF which are used in the de novo biosynthesis of purines and thymidylate, respectively. DHF is the byproduct of the catalytic activity of thymidylate synthase (TS) which catalyzes the conversion of dUMP to dTMP in a 5,10-methylene-THF-dependent reaction. Thus, DHFR is crucial for the recycling of THF cofactors that are essential for the biosynthesis of purine and pyrimidine nucleotides that are necessary for DNA replication. Hence, cells (e.g. CHO cells) that lack the DHFR gene (i.e. by targeted genomic deletion) can be used as recipients for the transfection of the DHFR gene in a medium that is free of nucleotides. After transfection, the cells can be subjected to a gradual increase in the concentrations of the antifolate MTX, a most potent DHFR inhibitor (Kd=1 pM), thereby forcing the cells to produce increased levels of DHFR. Upon multiple rounds of selection, the selectable marker DHFR frequently undergoes significant gene amplification. Furthermore, a mutant mouse DHFR with a major resistance to MTX has also been extensively used as a dominant selectable marker that markedly enhances the acquisition of high level MTX-resistance in transfectant cells. A major disadvantage of the DHFR/MTX selection system is that this technique utilizes a mutagenic cytotoxic agent, MTX, that can readily alter the genotype of the recipient cells. Additionally, specific safety measures may have to be taken to protect the persons handling such agents. This frequently results in MTX-resistant cell populations in which no expression of the target gene of interest is present due to loss of function mutations in the reduced folate carrier (RFC) and/or loss of RFC gene expression, both of which abolish MTX uptake. Another disadvantage is that the mutagenic drug MTX may readily contaminate the secreted overexpressed target product (e.g. a polypeptide like an antibody) contained in the growth medium thereby requiring labor intensive, time-consuming and expensive chromatographic methods necessary to rid off this mutagenic compound, MTX. In addition, the absence of MTX in the final product has to be demonstrated by respective assays.

(c) The reduced folate carrier selection system: The reduced folate carrier (RFC) is a ubiquitously expressed membrane glycoprotein that serves as the major transporter for the uptake of reduced folates such as 5-methyl-THF and 5-formyl-THF. However, RFC displays a very poor affinity for the oxidized folate, folic acid. Hence, cells that lack the expression of RFC or have been deleted for the genomic RFC locus can serve as recipients for the transfection of the selectable marker gene RFC under conditions in which reduced folates such 5-formyl-THF are gradually deprived from the growth medium thereby forcing the cells to express increased levels of the this folate transporter. There are several disadvantages for the RFC selection system: a) One must use RFC-null recipient cells in which the endogenous RFC locus has been knocked out or inactivated by targeted knockout or loss of function mutations. b) RFC has an extremely poor transport affinity for folic acid and thus this oxidized folate cannot be used for selection. c) As opposed to the current folate-receptor based system that is a unidirectional folate uptake system and which will be explained in detail below, RFC is a bi-directional folate transporter that exhibits equally potent import and export of folates. This implies that under conditions of folate deprivation, RFC overexpression may be detrimental to the recipient cells that further export folate via the overexpressed RFC.

The aim of the present invention is to provide a novel metabolic selection system that has certain advantages over the prior art selection systems mentioned above. The novel selection system is based upon the use of folates in the cell culture medium and on the presence of folate receptors introduced via an expression vector into the recombinant eukaryotic cell intended to produce a product of interest. This novel approach requires no prior deletion of an endogenous folate receptor (FR) gene. Following the introduction of a vector harboring both the FR selectable gene as well as the polynucleotide encoding a product of interest (like a polypeptide), cells are grown in a selective medium containing highly limiting concentrations of folates. Hence, only cells that markedly overexpress FR can take up sufficient folates to sustain cell growth, DNA replication and cellular proliferation, thereby allowing for overexpression of the target product of interest.

The oxidized folate, i.e. folic acid, as well as reduced derivatives of folic acid, known as reduced folates or tetrahydrofolates (THF) are a group of B-9 vitamins that are essential cofactors and/or coenzymes for the biosynthesis of purines, thymidylate and certain amino acids in eukaryotic, in particular mammalian, cells. THF cofactors are particularly crucial for DNA replication and hence cellular proliferation. Specifically, THF cofactors function as donors of one-carbon units in a series of interconnected metabolic pathways involving de novo biosynthesis of purines and thymidylate, amino acids as well as methyl group metabolism, including CpG island methylation of DNA. Specifically, THF cofactors including 10-formyl-THF (10-CHO-THF) contribute one-carbon units in two key de novo formyltransferase reactions involved in the de novo biosynthesis of purines. The first enzyme, glycinamide ribonucleotide transformylase (GARTF), is involved in the formation of the imidazole ring of purines, whereas the more downstream reaction mediated by 5-aminoimidazole-4-carboxamide ribonucleotide transformylase (AICARTF) yields the purine intermediate inosine 5'-monophosphate (IMP). The latter serves as a key precursor for the regulated biosynthesis of AMP and GMP. Furthermore, 5,10-methylene-THF (5,10-CH$_2$-THF), is another important THF coenzyme which functions as a crucial cofactor for the enzyme thymidylate synthase (TS). TS catalyzes the formation of thymidine monophosphate (dTMP) from dUMP. Hence, these folate-dependent enzymes are key mediators of the de novo biosynthesis of purine and thymine nucleotides essential for DNA replication. As such, these folate-dependent enzymes were identified as targets for the activity of folic acid antagonists known as antifolates. For example, the 4-amino folic acid analogue aminopterin and its homologue 4-amino-10-methylfolic acid, methotrexate (MTX) were the first class of antimetabolites that were introduced to the clinic for the chemotherapeutic treatment of childhood acute lymphoblastic leukemia (ALL). Antifolates are currently key components of different chemotherapeutic regimens currently used for the treatment of other human malignancies including osteosarcoma, breast cancer, primary central nervous system lymphoma, choriocarcinoma and gestational trophoblastic neoplasia.

In contrast to most prokaryotes, plants, fungi and certain protests which synthesize their own folates, mammals and other eukaryotic species are devoid of THF cofactor biosynthesis and must therefore obtain them from exogenous sources. Three independent transport systems are currently known to mediate the uptake of folates and antifolates in mammalian cells:

a) The predominant cellular transport system of reduced folate cofactors is the reduced folate carrier (RFC). The RFC (also known as solute carrier family 19 member 1, SLC19A1) is a ubiquitously expressed ~85 kDa membrane glycoprotein functioning as a bi-directional facilitative carrier that mediates the uphill transport of reduced folates by exchanging organic phosphates such as adenine nucleotides that are known to accumulate to very high intracellular levels as well as thiamine mono- and pyrophosphate. RFC displays a high-affinity for THF cofactors including leucovorin (5-formyl-THF; Kt=1 µM), while harboring only a very poor transport affinity (Kt=200-400 µM) for folic acid, an oxidized folate.

b) Another route of folate uptake is the proton-coupled folate transporter (PCFT, also known as SLC46A) which has recently been cloned. PCFT appears to be expressed independently of the RFC, functions optimally at acidic pH (5.5) and mediates the influx of both oxidized (e.g. folic acid) and THF cofactors (i.e. reduced folates) as well as various hydrophilic antifolates including MTX. PCFT, which shows an optimal transport of folates and antifolates at acidic pH (5.5) but none at physiological pH (7.4), has a key role in the absorption of both folates and antifolates in the upper small intestine.

c) The third transport route, on which the present invention is based, involves folate receptors (FRs). FRs are high-affinity folate-binding glycoproteins encoded by three distinct genes FRα (FR alpha), FRβ (FR beta) and FRγ (FR gamma). FRα □(or FR-alpha) is also known as Adult Folate Binding Protein or FDP, as Folate Receptor1 or FOLR (in mice folbp1), and as Ovarian cancer-Associated Antigen or MOv 18. FRβ (or FR beta) is also known as FOLR2 (fetal) and as FBP/PL-1(placenta). FRγ (or FR gamma) is also known as FOLR3 and as FR-G (reviewed by M. D. Salazar and M. Ratnam, Cancer Metastasis Rev. 2007 26(1), pp. 141-52.). The mature FRs, which are well-characterized, are homologous proteins with ~70-80% amino acid identity and contain 229 to 236 amino acids as well as two to three N-glycosylation sites. FRα (FR alpha) and FRβ (FR beta) are membrane-bound, in particular glycosylphosphatidylinositol (GPI)-anchored, cell surface glycoproteins, whereas FRγ is devoid of a GPI anchor and is a secreted protein. FRα (FR alpha) and FRβ (FR beta) display a high affinity for folic acid (Kd=0.1-1 nM), 5,10-dideazatetrahydrofolic acid (DDATHF; lometrexol; Ki=0.4-1.3 nM using [$^3$H]folic acid as a substrate) and BGC945 (which is a cyclopenta[g]quinazoline-based, thymidylate synthase inhibitor specifically transported solely via FRα (FR alpha) and not via the reduced folate carrier) (Kd=1 nM), but much lower affinity for MTX (Kd>100 nM). FR-dependent uptake of folate and antifolates proceeds via a classical mechanism of receptor-mediated endocytosis. Gene knockout studies have shown that FRα (FR alpha) (also known as Folbp1 in mice) is essential for early embryonic development and maternal folate supplementation rescued from in utero embryonic lethality and allowed for normal development.

There is an ongoing need for a safe, highly effective and cost-efficient selection system which overcomes one or more of the disadvantages of the selection systems known up to date.

SUMMARY OF THE INVENTION

The present invention relates to a eukaryotic expression vector comprising a first polynucleotide encoding a functional membrane-bound folate receptor and a second polynucleotide encoding a product of interest.

The present invention further relates to eukaryotic cells for which cellular viability is dependent on folic acid uptake, and into which the said expression vector has been stably introduced such that the functional folate receptor encoded by the vector is expressed by the cells.

Furthermore, the present invention relates to a selection method for providing a recombinant eukaryotic cell capable of stably expressing the product of interest in high yields.

The present invention can favorably be utilized in a process for production of the product of interest in high yields.

DETAILED DESCRIPTION OF THE INVENTION

In the course of the present invention, it has now surprisingly been found that a selection system for providing recombinant eukaryotic cells capable of producing a product of interest can be based on the limited availability of a folate in a cell culture medium. The system will be widely applicable, i.e. to a eukaryotic cell which cellular viability depends upon the uptake of a folate.

The novel system can be used for the accelerated selection, screening and establishment of eukaryotic, for example mammalian, cell clones that stably overexpress high levels of recombinant products in the absence of cytotoxic drugs. Even more, and in contrast to other known selection systems, there is no essential need (although sometimes feasible) for modified cells, provided e.g. by mutating or knocking out endogenous gene(s). Since e.g. FRα (FR alpha) displays a higher affinity for FA ($K_D$=0.1 nM) than, for example, RFC for leucovorin (Kt=1 µM), and transports folic acid into cells via a unidirectional pathway the present invention provides for the use of FRα (FR alpha) and other folate receptors as a markedly improved dominant metabolic selectable marker, in particular, via gradual folate (e.g. folic acid) deprivation from the growth medium. The novel folate-based selection is an excellent strategy that is well-suited for the accelerated, stable and high level overexpression of target proteins in cultured mammalian cells in the absence of cytotoxic drug selection as routinely used in various overexpression systems.

The novel selection system shows several important advantages over selection systems available in the prior art.

1. The selection system according to the present invention is a very rapid selection system: Within four weeks of folic acid deprivation, cell population or clonal cell derivatives expressing the target gene of interest can be readily isolated. This is in contradistinction to the GS system mentioned above which may require 2-6 months of selection and stabilization of the target gene.

2. The selection system according to the present invention does not require a genomic deletion or attenuation of the endogenous FRα (alpha), β (beta) or γ (gamma) genes prior to transfection and thus can be applied to any recipient cell even when some endogenous FR gene expression is present. This key advantage is based upon the fact that following FRα (FR alpha) transfection, cells can be exposed to an abrupt and severe deprivation of folates (e.g. folic acid) from the growth medium. Consequently, only transfectant cells which express significant amounts of the selectable FRα (FR alpha) marker can transport sufficient folate to sustain DNA replication and cellular proliferation. This occurs in the absence of any significant elevation in the expression of the endogenous FRα (FR alpha) gene. This is in contrast to the DHFR/MTX system mentioned above in which the recipient cells are frequently deleted for the endogenous DHFR gene (e.g. CHO DG44 cells and CHO Dux cells).

c) The selection system according to the present invention does not suffer from the loss of stringency of selection due to alleviation of the selective pressure via increased expression of alternative routes of folate uptake including increased expression of the endogenous RFC. This important advantage is due to the fact that whereas FRα (FR alpha) has an outstanding affinity for folic acid (Kd=0.1 nM), the RFC displays an extremely poor affinity for folic acid (Km=0.2-0.4 mM). In contrast, various prior art selection systems including the DHFR/MTX system can suffer from a severe loss of stringency of selection since upon MTX selection, MTX-resistant cells can be frequently obtained that have no or poor selectable marker expression. Instead, loss of function of the RFC, the primary MTX transporter may become a frequent mechanism of MTX resistance. This has been shown to be due to the frequent emergence of inactivating mutations in the RFC gene or severe loss of RFC gene expression.

d) The selection system according to the present invention does not use a cytotoxic drug and/or mutagenic compound such as MTX in the DHFR system or MSX in the GS system that can alter the genotype of the recipient cells as well as of the target gene of interest. Rather, the FR selection utilizes the principle of deprivation of a vitamin from the growth medium.

Accordingly, in one aspect the present invention thus relates to a eukaryotic expression vector comprising a first polynucleotide encoding a functional membrane-bound folate receptor (i.e. the selectable marker gene) and a second polynucleotide encoding a product of interest.

A functional membrane-bound folate receptor according to the present invention is particularly defined as a functional membrane-bound receptor capable of unidirectional import or uptake of a folate into a eukaryotic cell.

A folate according to the present invention can either be an oxidized folate (i.e. folic acid) or a reduced folate. In general, a folate may be useful within the present invention as long as such folate will be capable of being taken up into a eukaryotic cell by the functional membrane-bound folate receptor. A preferred example of an oxidized folate is folic acid. Preferred examples of reduced folates are 5-methyl-tetrahydrofolic acid, 5-formyl-tetrahydrofolic, 10-formyl-tetrahydrofolic acid and 5,10-methylene-tetrahydrofolic acid.

In a preferred embodiment, the expression vector of the present invention is capable of expressing both the functional membrane-bound folate receptor and the product of interest in a eukaryotic cell.

The product of interest encoded by the second polynucleotide can be any biological product capable of being produced by transcription, translation or any other event of expression of the genetic information encoded by the second polynucleotide. In this respect, the product will be an expression product. For example, in a preferred embodiment, such a product is selected from the group consisting of a polypeptide, a RNA, and a DNA. A "polypeptide" refers to a molecule comprising a polymer of amino acids linked together by peptide bond(s). The term "polypeptide" includes polypeptides of any length, which may be called "protein" in case of a larger molecule (comprising for example more than about 50 amino acids), or "peptide" in case of a smaller molecule (comprising for example 2-49 amino acids). The product can be a pharmaceutically or therapeutically active compound, or a research tool to be utilized in assays and the like. In a particularly preferred embodiment, the product is a polypeptide, preferably a pharmaceutically or therapeutically active polypeptide, or a research tool to be utilized in diagnostic or other assays and the like. In a most preferred embodiment the polypeptide is an immunoglobulin molecule or antibody, or a fragment (in particular a functional fragment) thereof, for example a chimeric, or a partly or totally humanized antibody. Such an antibody can be a diagnostic antibody, or a pharmaceutically or therapeutically active antibody. Typically, the product of interest will be heterologous to the eukaryotic host cell used for expression, which means that the host cell does not naturally or endogenously produce the product of interest before transfection. Rather, in order to achieve production or expression of the product of interest a polynucleotide encoding the product of interest has to be introduced into the eukaryotic host cell, in particular by transfection with an expression vector according to the present invention.

A vector according to the present invention can be present in linear form or, preferably, in circular form, e.g. a plasmid.

Vectors used for expression of polynucleotides of interest usually contain transcriptional control elements suitable to drive transcription such as e.g. promoters, enhancers, polyadenylation signals, transcription pausing or termination signals. If the desired product is a protein, suitable translational control elements are usually included in the vector, such as e.g. 5' untranslated regions leading to 5' cap structures suitable for recruiting ribosomes and stop codons to terminate the translation process. In particular, both the polynucleotide serving as the selectable marker gene as well as the polynucleotide encoding for the product of interest will be transcribed under the control of transcription elements present in appropriate promoters. The resultant transcripts of both the selectable marker gene and that of the product of interest harbor functional translation elements that facilitate substantial levels of protein expression (i.e. translation).

Accordingly, a preferred embodiment relates to an expression vector according to the present invention wherein the first polynucleotide and the second polynucleotide are under the control of distinct transcription promoters. In general, a promoter capable of promoting expression, in particular transcription, of the first and/or second polynucleotide in a eukaryotic will be suitable. In a preferred embodiment, the distinct transcription promoters are the same. In another preferred embodiment the distinct transcription promoters are different. Preferably, the transcription promoters are selected from the group consisting of an SV40 promoter, a CMV promoter, an EF1alpha promoter, a RSV promoter, a BROAD3 promoter, a murine rosa 26 promoter, a pCEFL promoter and a β-actin promoter. In a preferred embodiment thereof the promoter controlling the transcription of the first polynucleotide and/or second polynucleotide is CMV promoter or, mostly preferred, an SV40 promoter. In a particularly preferred embodiment the promoter controlling the transcription of the first polynucleotide is a SV40 promoter.

In another preferred embodiment of an expression vector of the present invention the first polynucleotide and the second polynucleotide are under the control of a common transcription promoter. Preferably, such transcription promoter is selected from the group consisting of an SV40 promoter, a CMV promoter, a RSV promoter, a BROAD3 promoter, a murine rosa 26 promoter, a pCEFL promoter and a β-actin promoter. In a further preferred embodiment thereof the common transcription promoter is an SV40 promoter. A further preferred embodiment of the expression vector having such a common transcription promoter comprises an IRES element functionally located between the first polynucleotide and the second polynucleotide.

The membrane bound folate receptor as introduced into the eukaryotic host cell by means of an expression vector utilized according to the present invention can be derived from any species as long as it will be functional within the present invention, i.e. compatible with the eukaryotic cell utilized. Preferably, a folate receptor derived from a mammalian species will be used, for a example derived from a rodent, or, mostly preferred, a human folate receptor. In general, the folate receptor introduced into the eukaryotic host cell and utilized as selection marker can be homologous or heterologous to an endogenous folate receptor of the host cell. If it is homologous it will be derived from the same species as the host cell, and may, for example, be identical to an endogenous folate receptor of the host cell. If it is heterologous it will be derived from another species than the host cell, and may thus be different from an endogenous folate receptor of the host cell. Typically, the introduced folate receptor utilized as the selection marker will be heterologous to the host cell. For example a human-derived folate receptor may be used as selection marker for a rodent host cell, e.g. a CHO cell.

Preferably, the functional membrane-bound folate receptor encoded by the first polynucleotide of an expression vector of the present invention is selected from the group consisting of the folate receptor alpha (FRα), the folate receptor beta (FRβ), and a functional mutant thereof. A functional mutant comprises a derivative of a folate receptor which is functional in a physiological manner, i.e. capable of being uptaken by the eukaryotic cell and contributing to the cell's viability via the cell's folate metabolism. For example, a mutant form of the folate receptor will comprise one or more amino acid mutation(s), like a substitution, deletion and/or addition, as well as a chemical derivative, where a chemical moiety, like a polymer, for example a polyethylene glycol structure (PEG), is attached to the folate receptor. Preferably, the folate receptor encoded by the first polynucleotide is a human folate receptor alpha (hFRα), a human folate receptor beta (hFRβ), or a functional mutant thereof. Most preferred is a human folate receptor alpha (hFRα), preferably having the following amino acid sequence (SEQ ID NO 1, 1-letter code, shown in direction from N-terminus to C-terminus):

MAQRMTTQLLLLLVWVAVVGEAQTRIAWARTELLNVCMNAKHHKEKPGPE

DKLHEQCRPWRKNACCSTNTSQEAHKDVSYLYRFNWNHCGEMAPACKRHF

IQDTCLYECSPNLGPWIQQVDQSWRKERVLNVPLCKEDCEQWWEDCRTSY

TCKSNWHKGWNWTSGFNKCAVGAACQPFHFYFPTPTVLCNEIWTHSYKVS

NYSRGSGRCIQMWFDPAQGNPNEEVARFYAAAMSGAGPWAAWPFLLSLAL

MLLWLLS

Another preferred embodiment relates to a human folate receptor beta (hFRβ) having the following amino acid sequence (SEQ ID NO 2, 1-letter code, shown in direction from N-terminus to C-terminus):

MVWKWMPLLLLLVCVATMCSAQDRTDLLNVCMDAKHHKTKPGPEDKLHDQ

CSPWKKNACCTASTSQELHKDTSRLYNFNWDHCGKMEPACKRHFIQDTCL

YECSPNLGPWIQQVNQTWRKERFLDVPLCKEDCQRWWEDCHTSHTCKSNW

HRGWDWTSGVNKCPAGALCRTFESYFPTPAALCEGLWSHSYKVSNYSRGS

GRCIQMWFDSAQGNPNEEVARFYAAAMHVNAGEMLHGTGGLLLSLALMLQ

LWLLG

In an alternative, the present invention relates to a folate receptor which in its natural environment is not membrane-bound. Such a non-membrane bround receptor can be mutated in order to become membrane-bound, for example by providing a fusion protein between the non membrane-bound folate receptor and a transmembrane region of another polypeptide. Likewise, other mutant forms are possible which would be readily available for a person skilled in the art. Preferred examples in this respect would be based on the soluble folate receptor gamma (FRγ), preferably the human soluble folate receptor gamma (FRγ). In a most preferred embodiment thereof, the human soluble folate receptor gamma (FRγ) would have the following amino acid sequence (SEQ ID NO 3, 1-letter code, shown in direction from N-terminus to C-terminus):

```
MDMAWQMMQL LLLALVTAAG SAQPRSARAR TDLLNVCMNA

KHHKTQPSPE DELYGQCSPW KKNACCTAST SQELHKDTSR

LYNFNWDHCG KMEPTCKRHF IQDSCLYECS PNLGPWIRQV

NQSWRKERIL NVPLCKEDCE RWWEDCRTSY TCKSNWHKGW

NWTSGINECP AGALCSTFES YFPTPAALCE GLWSHSFKVS

NYSRGSGRCI QMWFDSAQGN PNEEVAKFYA AAMNAGAPSR

GIIDS
``` which then may be mutated or otherwise genetically altered or derivatized to form a functional membrane-bound folate receptor capable of folate uptake within the context of the present invention.

In a further aspect, the expression vector according to the present invention can additionally comprise one or more further polynucleotide(s) encoding one or more additional selection marker(s). Accordingly, in a preferred embodiment co-selection utilizing the folate system of the present invention together with one or more different selection system(s) (e.g. neo/G418) can be applied to provide optimal performance.

In another aspect, the present invention relates to a eukaryotic cell for which cellular viability is dependent on folate uptake, and into which eukaryotic cell a first polynucleotide located on an expression vector and encoding a functional membrane-bound folate receptor and a second polynucleotide located on an expression vector and encoding the product of interest have been stably introduced, wherein the first polynucleotide and the second polynucleotide are located on the same expression vector or on separate an expression vectors. In a preferred embodiment thereof, the functional membrane-bound folate receptor and the product of interest are expressed by the eukaryotic cell.

In addition to the functional membrane-bound folate receptor introduced into the cell line via an expression vector, the eukaryotic cell according to the present invention can comprise at least one endogenous functional unidirectional functional folate transport system, in particular one or more endogenous functional membrane-bound folate receptor(s). It is an advantage of the present invention that the method of selection as described herein below can be utilized even in the presence of such endogenous unidirectional functional folate transport system, i.e. where such endogenous system is retained. Accordingly, a further preferred embodiment relates to the eukaryotic cell of the present invention relates, comprising at least one endogenous unidirectional functional folate transport system, wherein such endogenous unidirectional functional folate transport system preferably comprises at least one endogenous functional membrane-bound folate receptor. In a preferred embodiment thereof, the endogenous functional membrane-bound folate receptor is selected from the group consisting of the folate receptor alpha (FRa) and the folate receptor beta (FRβ).

Another preferred embodiment relates to a eukaryotic cell according to the present invention, wherein the endogenous unidirectional functional folate transport system, for example comprising at least e.g. one endogenous functional membrane-bound folate receptor, is lacking full activity, i.e. is attenuated. Such attenuation can be provided for example by any type of mutagenesis of the endogenous folate transport system in question, e.g. the endogenous functional membrane-bound folate receptor, for example by point mutation, gene disruption, and the like. The attenuation can be a partial or complete. In the latter case the eukaryotic cell according to the present invention does not comprise an endogenous functional unidirectional functional folate transport system, e.g. an endogenous functional membrane-bound folate receptor. Accordingly, a preferred embodiment the present invention relates to such a eukaryotic cell wherein an expression vector of the present invention has been stably introduced, and which cell is lacking full activity of at least one endogenous functional membrane-bound folate receptor.

With respect to the expression vector introduced into said host cell any expression vector of the present invention, including its preferred embodiments, as described herein, can be utilized. In a preferred embodiment of the eukaryotic cell of the present invention the first polynucleotide encoding a functional membrane-bound folate receptor and the second polynucleotide encoding the product of interest are located on the same expression vector. Preferably, such expression vector is and expression vector according to the present invention, i.e. as described herein.

The eukaryotic cell according to the present invention is, preferably, selected from the group consisting of a mammalian cell, an insect cell, a plant cell and a fungi cell. With respect to fungi cells and plant cells, which usually are prototrophic for folates (i.e. such cells can autonomously synthesize their own folates necessary for their cellular viability, i.e. cellular growth and proliferation). The present invention encompasses in particular such fungi and plant cells which may become auxotrophic for folates. This may be for example due to genetic manipulation, i.e. cells are now unable to synthesize sufficient amounts of folates necessary for their cellular viability. For example, the capacity of such fungi or plant cells to endogenously biosynthesize folates, e.g. via an appropriate metabolic pathway, will be inactivated, e.g. by gene disruption or gene silencing of appropriate target genes, or inhibition of key enzymes, etc.

In a preferred embodiment thereof the eukaryotic cell is a mammalian cell. Preferably, such mammalian cell is selected from the group consisting of a rodent cell, a human cell and a monkey cell. Particularly preferred is a rodent cell, which preferably is selected from the group consisting of a CHO cell, a BHK cell, a NSO cell, a mouse 3T3 fibroblast cell, and a SP2/0 cell. A most particularly preferred rodent cell is a CHO cell. Also preferred is a human cell, which, preferably, is selected from the group consisting of a HEK293 cell, a MCF-7 cell, a PerC6 cell, and a HeLa cell. Further preferred is monkey cell, which, preferably, is selected from the group consisting of a COS-1, a COS-7 cell and a Vero cell.

In another embodiment the present invention relates to a process for production of a eukaryotic cell according to the present invention, said process comprising providing an eukaryotic cell for which cellular viability is dependent upon folate uptake, and introducing a first polynucleotide located on an expression vector and encoding the functional membrane-bound folate receptor and a second polynucleotide located on an expression vector and encoding the product of interest, wherein the first polynucleotide and the second polynucleotide are located on the same expression vector or on separate an expression vectors. In a preferred embodiment, the first polynucleotide and the second polynucleotide are located on the same expression vector which, in a most preferred embodiment, is an expression vector according to the present invention, i.e. as disclosed herein.

A yet other aspect of the present invention relates to a method for selection of a eukaryotic cell capable of stably expressing a product of interest encoded by an expression vector which has been introduced into the cell, comprising (i) providing a plurality of eukaryotic cells for which cellular viability is dependent upon folate uptake, and into which cells a first polynucleotide located on an expression vector and encoding a functional membrane-bound folate receptor and a second polynucleotide located on an expression vector and encoding the product of interest have been introduced, wherein the first polynucleotide and the second polynucleotide are located on the same expression vector or on separate expression vectors, (ii) culturing said plurality of eukaryotic cells in a cell culture medium having a limiting concentration of a folate, thereby obtaining a eukaryotic cell wherein stable expression of the product of interest is achieved. In principle, such folate can be an oxidized folate or a reduced folate. Preferred is an oxidized folate, which in particular is folic acid.

With respect to the limiting amount of a folate the suitable concentration in the medium can be determined by a person skilled in the art in accordance with the requirements of the host cell and the stringency of the selection condition to be applied. In case that folic acid is used as the folate, for example with a CHO host cell, a suitable concentration of folic acid in the cell culture medium for a stringent selection process would be about 100 nM or lower, preferably about 30 nM or lower, or about 10 nM or lower. For example, a suitable concentration of folic acid can have any value in the range of 0.001 nM-100 nM, preferably in the range of 0.01 nM-100 nM, more preferably in the range of 0.1 nM-100 nM or in the range of 1 nM-100 nM. Likewise preferred is the range of 0.001 nM-30 nM, the range of 0.01 nM-30 nM, the range of 0.1 nM-30 nM, the range of 1 nM-30 nM, or the range of 3 nM-10 nM. For example, the folic acid concentration in the cell culture medium suitable for selection can be 1 nM, 3 nM, 10 nM or 30 nM.

In case that a reduced folate like leucovorin will be used in the selection process the concentration thereof again can be determined by a person skilled in the art in accordance with the requirements of the host cell and the stringency of the selection condition to be applied. Such concentration of leucoverin in the cell culture medium can be for example be in the range of 0.2 nM-2 nM for a stringent selection process.

In a further embodiment thereof, the method for selection further comprises identifying and isolating a eukaryotic cell wherein stable expression of the product of interest is achieved.

In a most preferred embodiment of the method for selection, the plurality of eukaryotic cells is composed of eukaryotic cells according to the present invention, i.e. as disclosed herein.

Further preferred embodiments of this aspect of the represent invention are described herein, in particular with respect to the eukaryotic cell and the expression vector.

Another embodiment of the present invention relates to a process for production of a product of interest, comprising (i) performing a method of selection according to the present invention, i.e. as disclosed herein, (ii) and isolating the product of interest from said cell culture medium or from said cell.

Again, preferred embodiments of this aspect of the represent invention are described herein, in particular with respect to the eukaryotic cell and the expression vector.

The product of interest, for example a polypeptide, produced in accordance with the invention may be recovered, further purified and isolated by methods known in the art. For example, the polypeptide may be recovered from the nutrient medium by conventional procedures including, but not limited to, centrifugation, filtration, ultra-filtration, extraction or precipitation. Purification may be performed by a variety of procedures known in the art including, but not limited to, chromatography (e.g. ion exchange, affinity, hydrophobic, chromatofocusing, and size exclusion), electrophoretic procedures (e.g., preparative isoelectric focusing), differential solubility (e.g. ammonium sulfate precipitation) or extraction.

A yet further aspect of the present invention relates to the use of a functional membrane-bound folate receptor as a selection marker for selection of a eukaryotic cell, for which eukaryotic cell cellular viability is dependent on the uptake of folate, and which eukaryotic cell being capable of stably expressing a product of interest. Within a preferred embodiment of such use, the folate receptor is selected from the group consisting of the folate receptor alpha (FRα), the folate receptor beta (FRβ), and a fuctional mutant thereof. Preferably, the folate receptors utilized within this aspect of the present invention are the respective human folate receptors, the human folate acid receptor alpha (FRα) being preferred. Further preferred embodiments of this aspect of the represent invention are described herein, in particular with respect to the eukaryotic cell and the expression vector.

The full contents of the texts and documents as mentioned herein are incorporated herein by reference.

The following examples serve to illustrate the present invention without in any way limiting the scope thereof. In particular, the examples relate to preferred embodiments of the present invention.

EXAMPLES

In general, the materials mentioned herein, such as reagents, are familiar to the skilled person, commercially available and can be used in accordance with the manufacturer's instructions.

Example 1

High-Level Expression of a Recombinant Antibody Utilizing the Folate-Receptor Based Selection System

Example 1.1

Expression Vectors

A plasmid vector (i.e. the test vector), suitable for expression in eukaryotic cells, in particular CHO cells, harboring both (i) an expression cassette which comprises a polynucleotide encoding the heavy and light chains of a secreted recombinant human antibody of IgG1 type, and (ii) an distinct expression cassette which comprises a polynucleotide encoding a human folic acid receptor alpha (hFRα) as selectable marker gene, is constructed to explore the efficiency of selection of hFRalpha (hFRα)-transfected cells under limiting concentrations of a folate, i.e. folic acid, in the culture medium. Expression of the human folic acid receptor alpha (hFRa) is under control of an SV40 promoter and a standard (SV40) polyadenylation signal. Expression of the recombinant antibody is under control of a CMV promoter and a standard (SV40) polyadenylation signal. As a control (i.e. the control vector), a similar expression vector is used, encoding the same antibody, and lacking the hFRalpha (hFRα) expression cassette, but containing a neomycin phosphotransferase gene as a selectable marker.

Example 1.2

Cells and Growth Conditions

Chinese hamster ovary cells derived from strain CHO-K1 are maintained under suspension culture conditions in suitable chemically defined growth medium containing 2.3 μM (microM) folic acid.

For analysis of folic acid dependency of cell survival, a folic acid starvation experiment is done using folic acid concentrations ranging from 2300 nM to 0.1 nM. Cells are cultivated in such medium and cell viability is analyzed to quantify the percentage of surviving cells. Table 1 summarizes the results obtained with the CHO-K1 cell line mentioned above.

TABLE 1

Survival of CHO cells at different folic acid concentrations:

| FA Concentration [nM] | Precentage of Survival |
| --- | --- |
| 0.1 | 2.08 |
| 1 | 2.45 |
| 3 | 2 |
| 10 | 2.7 |
| 30 | 6.8 |
| 100 | 55.5 |
| 300 | 88.6 |
| 1000 | 100.8 |
| 2300 | 100 |

These results indicate that for this specific host cell line folic acid concentrations below 100 nM, preferably below 30 nM should be suitable to generate significant selection pressure for folic acid receptor based selection of stably transfected cells.

Example 1.3

Transfection and Selection

Cells are transfected by electroporation either with the test vector containing a hFRalpha (hFRα) expression cassette or the control vector lacking the hFRalpha hFRα. The transfectant cells are subsequently grown under suspension culture conditions in 125 ml shake flasks in medium supplemented with an appropriate concentration of glutamine and 2.3 μM (microM) folic acid. Forty eight hours after transfection, cells are transferred to a medium containing a limited amount of folic acid, namely 10 nM or 1 nM folic acid to initiate the selection process according to the invention in 24-well plates for samples transfected with the test vector. In addition, cells transfected with the control plasmid are selected by adding a selection agent, namely 0.8 mg/mL G418, to a medium containing 2.3 μM (microM) folic acid (i.e. control 1) or cultured in the absence of any selection (i.e. control 2). Cells which have successfully recovered from this selection scheme are transferred to 6-well plates and further expanded in shake flasks for analysis of antibody production levels.

Example 1.4

Analysis of Antibody Production

From the transfectant and folic acid deprived cell populations, overconfluent batch cultures in shake flasks are prepared to analyze antibody expression levels. Cells are seeded at $2 \times 10^5$ cells/mL in medium containing 2.3 μM (microM) folic acid and incubated under suspension culture (i.e. shaker) conditions. At day 14, the supernatant of the cell culture is harvested and analyzed for antibody levels using a protein-A HPLC methodology, i.e. an affinity-type of purification. IgG molecules specifically bind to the column, mainly via their Fc-part, while other proteins pass the column without interacting with the matrix. Under low pH conditions, captured IgG proteins are eluted from the column, quantified via UV absorption measurement, and, where necessary, further purified and isolated.

Example 1.5

Results

The aim of this approach is to provide a proof of concept that a folate gene, in particular the hFRalpha (hFRα) gene, can serve as a selectable marker under conditions of folate deprivation thereby selecting cells that co-overexpress a product of interest, e.g a monoclonal antibody. As a control, a vector containing a neomycin-resistance gene as a selectable marker is also used. After transfection, cells are subjected to a stringent selection by abruptly reducing the folic acid concentrations in the medium from 2.3 μM (microM) to 10 nM or 1 nM. Cells transfected with a plasmid harboring the folic acid receptor readily recover under conditions of folate deprivation and can be further expanded in the selective medium. In contrast, in the case of the control vector, the concentration of folic acid remains unchanged, but either a selection pressure with G418 or no selection pressure at all are applied. The selected cell populations are then analyzed for antibody production using overgrown (i.e. overconfluent) suspension (i.e. shake) flask cultures in medium containing 2.3 μM (microM) folic acid. The concentration of antibody in the culture medium is then determined at day 14. As shown in Table 1 below, cells transfected with the plasmid containing the folic acid receptor and selected by reducing folic acid availability, overexpress the recombinant antibody. The amount of antibody produced by these transfectant cell populations is higher compared to the cells transfected with the control vector and selected with G418. As a further control, when no selection pressure is applied, cells providing no antibody production are obtained. These data provide the proof of concept that the current folic acid receptor gene approach can be readily applied as a standalone dominant metabolic selectable marker to rapidly establish cells overexpressing a recombinant product of interest.

TABLE 2

($C_{Folic\ acid}$: concentration of folic acid in the medium during selection; $C_{G418}$: concentration of G418 in the medium during selection; $C_{mAb}$: concentration of the secreted antibody in the medium of overgrown cultures)

| Vector | $C_{Folic\ acid}$ (nM) | $C_{G418}$ (mg/ml) | $C_{mAb}$ (mg/l) |
|---|---|---|---|
| Test vector (hFRalpha (hFRα)) | 10 | none | 25 |
|  | 1 | none | 24 |
| Control vector (Neo) | 2300 | 0.8 | 8 |
|  | 2300 | none | 0 |

Example 2

Recombinant Antibody Production Levels Increase as a Function of the Decrease in Folic Acid Concentration in the Growth Medium

Example 2.1

Expression Vector

A plasmid vector (i.e. the test vector) as described in Example 1.1 above is provided.

Example 2.2

Cells and Growth Conditions

Chinese hamster ovary cells derived from strain CHO-K1 are maintained under monolayer culture conditions in chemically defined growth medium RPMI-1640 containing 2.3 µM (microM) folic acid. The cells are lacking RFC transporter activity, as disclosed elsewhere (Assaraf, Y. G. and Schimke, R. T. (1987) *Proc. Natl. Acad. Sci. USA* 84, 7154-7158; Rothem, L., et al., *Mol. Pharmacol.* 68: 616-624). Such a RFC-deficient cell is used to avoid a potential by-pass of the folic acid starvation by this further carrier system in this example.

Example 2.3

Transfection and Selection

RFC-deficient C15 cells are transfected with the test vector by electroporation. Forty eight hours after transfection, cells are propagated in folic acid-free medium supplemented with 30 nM folic acid in order to promote the expression of both the selectable marker as well as the recombainant antibody and subseqeuntly subjected for dilution cloning. Cells are diluted to a final density of 5 cells/ml and seeded at 100 µl/well in 96-well plates (i.e. 0.5 cells/well). Clones are then maintained in a medium containing 0.25 nM folic acid and 500 µg/ml G418. The co-selection utilizing the folate system of the present invention together with an additional selection system (i.e. neo/G418) is applied to provide optimal performance of the selection process. Clones with the highest levels of antibody production are then grown under low folic acid concentrations (i.e. 1200 pM, 600 pM, and 60 pM) to further support and establish antibody overexpression. This is corroborated by further analysis of antibody expression in the various clones.

Example 2.4

Analysis of Antibody Production

The analysis of antibody production is performed in principle as outlined in Example 1.4 above. The concentration of the secreted antibody is monitored using an ELISA assay as follows: Maxisorp microplates are coated with an anti-human IgG. Following blocking with a buffer containing bovine serum albumin (BSA) and several washes, multiple dilutions of the secreted antibody samples are added. Then, a peroxidase-conjugated second antibody consisting of goat anti-human IgG-peroxidase is added. Finally, a colorimetric peroxidase substrate is added following which the resultant dye concentration is determined in each well spectrophotometrically and then compared to standard concentrations of known IgG concentrations.

2.5 Results

As depicted in Table 2 below, the levels of recombinant antibody production correlate with the stringency of folic acid deprivation. Hence, antibody production levels increase as the concentration of folic acid concentration is decreased in the medium. These results further corroborate the proof of concept that the hFRalpha (hFRa) gene is an efficient selectable marker that can be used for the overexpression of recombinant proteins under conditions of folate deprivation.

TABLE 3

($C_{Folic\ acid}$: concentration of folic acid in the medium; $C_{mAb}$: concentration of the secreted antibody in the medium)

| $C_{Folic\ acid}$ (pM) | $C_{mAb}$ (µg/L) |
|---|---|
| 60 | 216 ± 30 |
| 600 | 138 ± 15 |
| 1200 | 19 ± 8 |

The invention claimed is:

1. A method for selection of a CHO cell capable of stably expressing a product of interest encoded by an expression vector which has been introduced into the cell, comprising
   (i) providing a plurality of CHO cells for which cellular viability is dependent upon folate uptake, and into which cells a first polynucleotide located on an expression vector and encoding a functional membrane-bound folate receptor alpha as selection marker and a second polynucleotide located on an expression vector and encoding the product of interest have been introduced, wherein the first polynucleotide and the second polynucleotide are located on the same expression vector or on separate expression vectors,
   (ii) culturing said plurality of CHO cells in a cell culture medium having a limiting concentration of a folic acid, wherein the concentration in the cell culture medium is from 0.001 nM to 100 nM, thereby obtaining a CHO cell wherein stable expression of the product of interest is achieved, and
   (iii) identifying and isolating a CHO cell wherein stable expression of the product of interest is achieved.

2. The method according to claim 1, wherein the plurality of CHO cells are CHO cells for which cellular viability is dependent on folate uptake and into which a first polynucleotide located on an expression vector and encoding a functional membrane-bound folate receptor alpha as a selection marker and a second polynucleotide located on an expression vector and encoding a product of interest have been stably introduced, wherein the first polynucleotide and the second polynucleotide are located on the same expression vector.

3. A process for production of a product of interest, comprising
   (i) performing a method of selection according to claim 1,
   (ii) and isolating the product of interest from said cell culture medium or from said cell.

4. The process of claim 3, wherein the product of interest is expressed from a eukaryotic expression vector that comprises a first polynucleotide encoding a functional membrane-bound folate receptor alpha and a second polynucleotide encoding the product of interest.

5. The process of claim 3, wherein the product of interest is a polypeptide.

6. The process of claim 5, wherein the product of interest is a pharmaceutically or therapeutically active polypeptide.

7. The method of claim 1, wherein the first polynucleotide and the second polynucleotide are each operably linked to its distinct transcription promotors.

8. The method of claim 7, wherein the transcription promoters are the same.

9. The method of claim 7, wherein the transcription promoters are different.

10. The method of claim 7, wherein the promoter controlling the transcription of the first polynucleotide is an SV40 promoter.

11. The method of claim 1, wherein the first polynucleotide and the second polynucleotide are under the control of a common transcription promoter.

12. The method of claim 11, wherein the common transcription promoter is an SV40 promoter.

13. The method of claim 11, wherein said vector comprises an IRES element functionally located between the first polynucleotide and the second polynucleotide.

14. The method of claim 1, wherein the functional membrane-bound folate receptor alpha encoded by the first polynucleotide is a human folate receptor alpha (FRα).

15. The method of claim 2, wherein the CHO cells lack full activity of at least one endogenous functional membrane-bound folate receptor.

16. The method of claim 1, wherein the concentration of folic acid in the cell culture medium is selected from 0.01 nM to 100 nM, 0.1 nM to 100 nM, 1 nM to 100 nM, 1 nM to 30 nM and 3 nM to 10 nM.

17. The process of claim 1, wherein the endogenous folate receptor alpha gene of the cell is not deleted or attenuated prior to transfection.

* * * * *

SEQUENCE LISTING

<160> NUMBER OF SEQ ID NOS: 3

<210> SEQ ID NO 1
<211> LENGTH: 257
<212> TYPE: PRT
<213> ORGANISM: Homo sapiens

<400> SEQUENCE: 1

Met Ala Gln Arg Met Thr Thr Gln Leu Leu Leu Leu Leu Val Trp Val
1               5                   10                  15

Ala Val Val Gly Glu Ala Gln Thr Arg Ile Ala Trp Ala Arg Thr Glu

```
                  20                  25                  30
Leu Leu Asn Val Cys Met Asn Ala Lys His His Lys Glu Lys Pro Gly
             35                  40                  45
Pro Glu Asp Lys Leu His Glu Gln Cys Arg Pro Trp Arg Lys Asn Ala
         50                  55                  60
Cys Cys Ser Thr Asn Thr Ser Gln Glu Ala His Lys Asp Val Ser Tyr
 65                  70                  75                  80
Leu Tyr Arg Phe Asn Trp Asn His Cys Gly Glu Met Ala Pro Ala Cys
                 85                  90                  95
Lys Arg His Phe Ile Gln Asp Thr Cys Leu Tyr Glu Cys Ser Pro Asn
                100                 105                 110
Leu Gly Pro Trp Ile Gln Gln Val Asp Gln Ser Trp Arg Lys Glu Arg
            115                 120                 125
Val Leu Asn Val Pro Leu Cys Lys Glu Asp Cys Glu Gln Trp Trp Glu
        130                 135                 140
Asp Cys Arg Thr Ser Tyr Thr Cys Lys Ser Asn Trp His Lys Gly Trp
145                 150                 155                 160
Asn Trp Thr Ser Gly Phe Asn Lys Cys Ala Val Gly Ala Ala Cys Gln
                165                 170                 175
Pro Phe His Phe Tyr Phe Pro Thr Pro Thr Val Leu Cys Asn Glu Ile
                180                 185                 190
Trp Thr His Ser Tyr Lys Val Ser Asn Tyr Ser Arg Gly Ser Gly Arg
            195                 200                 205
Cys Ile Gln Met Trp Phe Asp Pro Ala Gln Gly Asn Pro Asn Glu Glu
        210                 215                 220
Val Ala Arg Phe Tyr Ala Ala Met Ser Gly Ala Gly Pro Trp Ala
225                 230                 235                 240
Ala Trp Pro Phe Leu Leu Ser Leu Ala Leu Met Leu Leu Trp Leu Leu
                245                 250                 255
Ser

<210> SEQ ID NO 2
<211> LENGTH: 255
<212> TYPE: PRT
<213> ORGANISM: Homo sapiens

<400> SEQUENCE: 2

Met Val Trp Lys Trp Met Pro Leu Leu Leu Leu Val Cys Val Ala
 1               5                  10                  15
Thr Met Cys Ser Ala Gln Asp Arg Thr Asp Leu Leu Asn Val Cys Met
             20                  25                  30
Asp Ala Lys His His Lys Thr Lys Pro Gly Pro Glu Asp Lys Leu His
         35                  40                  45
Asp Gln Cys Ser Pro Trp Lys Lys Asn Ala Cys Cys Thr Ala Ser Thr
     50                  55                  60
Ser Gln Glu Leu His Lys Asp Thr Ser Arg Leu Tyr Asn Phe Asn Trp
 65                  70                  75                  80
Asp His Cys Gly Lys Met Glu Pro Ala Cys Lys Arg His Phe Ile Gln
                 85                  90                  95
Asp Thr Cys Leu Tyr Glu Cys Ser Pro Asn Leu Gly Pro Trp Ile Gln
                100                 105                 110
Gln Val Asn Gln Thr Trp Arg Lys Glu Arg Phe Leu Asp Val Pro Leu
            115                 120                 125
Cys Lys Glu Asp Cys Gln Arg Trp Trp Glu Asp Cys His Thr Ser His
```

```
                    130                 135                 140
Thr Cys Lys Ser Asn Trp His Arg Gly Trp Asp Trp Thr Ser Gly Val
145                 150                 155                 160

Asn Lys Cys Pro Ala Gly Ala Leu Cys Arg Thr Phe Glu Ser Tyr Phe
                    165                 170                 175

Pro Thr Pro Ala Ala Leu Cys Glu Gly Leu Trp Ser His Ser Tyr Lys
                180                 185                 190

Val Ser Asn Tyr Ser Arg Gly Ser Gly Arg Cys Ile Gln Met Trp Phe
                195                 200                 205

Asp Ser Ala Gln Gly Asn Pro Asn Glu Glu Val Ala Arg Phe Tyr Ala
                210                 215                 220

Ala Ala Met His Val Asn Ala Gly Glu Met Leu His Gly Thr Gly Gly
225                 230                 235                 240

Leu Leu Leu Ser Leu Ala Leu Met Leu Gln Leu Trp Leu Leu Gly
                    245                 250                 255

<210> SEQ ID NO 3
<211> LENGTH: 245
<212> TYPE: PRT
<213> ORGANISM: Homo sapiens

<400> SEQUENCE: 3

Met Asp Met Ala Trp Gln Met Met Gln Leu Leu Leu Leu Ala Leu Val
1               5                   10                  15

Thr Ala Ala Gly Ser Ala Gln Pro Arg Ser Ala Arg Ala Arg Thr Asp
                20                  25                  30

Leu Leu Asn Val Cys Met Asn Ala Lys His His Lys Thr Gln Pro Ser
                35                  40                  45

Pro Glu Asp Glu Leu Tyr Gly Gln Cys Ser Pro Trp Lys Lys Asn Ala
            50                  55                  60

Cys Cys Thr Ala Ser Thr Ser Gln Glu Leu His Lys Asp Thr Ser Arg
65                  70                  75                  80

Leu Tyr Asn Phe Asn Trp Asp His Cys Gly Lys Met Glu Pro Thr Cys
                85                  90                  95

Lys Arg His Phe Ile Gln Asp Ser Cys Leu Tyr Glu Cys Ser Pro Asn
                100                 105                 110

Leu Gly Pro Trp Ile Arg Gln Val Asn Gln Ser Trp Arg Lys Glu Arg
            115                 120                 125

Ile Leu Asn Val Pro Leu Cys Lys Glu Asp Cys Glu Arg Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Ile Asn Glu Cys Pro Ala Gly Ala Leu Cys Ser
                165                 170                 175

Thr Phe Glu Ser Tyr Phe Pro Thr Pro Ala Ala Leu Cys Glu Gly Leu
                180                 185                 190

Trp Ser His Ser Phe Lys Val Ser Asn Tyr Ser Arg Gly Ser Gly Arg
                195                 200                 205

Cys Ile Gln Met Trp Phe Asp Ser Ala Gln Gly Asn Pro Asn Glu Glu
                210                 215                 220

Val Ala Lys Phe Tyr Ala Ala Ala Met Asn Ala Gly Ala Pro Ser Arg
225                 230                 235                 240

Gly Ile Ile Asp Ser
                245
```